US006696268B1

(12) United States Patent
Shaw et al.

(10) Patent No.: US 6,696,268 B1
(45) Date of Patent: Feb. 24, 2004

(54) PRODUCTION AND USE OF ANTIMICROBIAL AGENTS

(75) Inventors: William Vare Shaw, Glasgow (GB); Ann Lewendon, Glasgow (GB)

(73) Assignee: Pantherix, Ltd. (GB)

( * ) Notice: Subject to any disclaimer, the term of this patent is extended or adjusted under 35 U.S.C. 154(b) by 0 days.

(21) Appl. No.: 09/787,465

(22) PCT Filed: Sep. 21, 1999

(86) PCT No.: PCT/GB99/03132

§ 371 (c)(1),
(2), (4) Date: Mar. 21, 2001

(87) PCT Pub. No.: WO00/17387

PCT Pub. Date: Mar. 30, 2000

(30) Foreign Application Priority Data

Sep. 21, 1998 (GB) ............................................ 98205388

(51) Int. Cl.[7] .......................... C12Q 1/18; C12N 15/09; C12N 15/70; C12N 15/00; C07H 21/04
(52) U.S. Cl. ........................ 435/32; 435/69.3; 435/325; 435/320.1; 536/23.7
(58) Field of Search ......................... 435/32, 325, 69.3, 435/320.1; 536/23.7

(56) References Cited

PUBLICATIONS

Geerlof et al., "Purification and Characterization of PPAT from *E.coli*", The journal of Biochemical Chemistry, vol. 274, No. 38, pp. 27105–27111, 1999.*

Van de Loo et al., Proc. Natl. Acad. Sci , vol. 92, pp. 6743–6747, 1995.*

Broun et al. , Science, vol. 282, pp. 1315–1317, 1998.*

Martin et al., "Separate Enzymes Catalyze the Final Two Steps of Coenzyme A . . . ",Biochemical and Biophysical Research Communications vol. 192, No. 3, pp. 1155–1161, 1993.*

Jackowski, S. et al. (Jun. 4, 1984) "Metabolism of 4'–phosphopantetheine in *Escherichia coli*" *Chemical Abstracts*, vol. 100(23), abstract No. 188569c.

Izard, Tina and Arie Geerlof (1999) "The crystal structure of a novel bacterial adenyltransferase reveals half of sites reactivity" *The EMBO Journal* 18(8):2021–2030.

Link, Andrew J., Dereth Phillips, George M. Church (Oct. 1977) "Methods for Generating Precise Deletions and Insertions in the Genome of Wild–Type *Escherichia coli*: Application to Open Reading Frame Characterization" *Journal of Bacteriology* 179(20):6228–6237.

Jackowski, Suzanne and Charles O. Rock (Apr. 1984) "Metabolism of 4'–Phosphopantetheine in *Escherichia coli*" *Journal of Bacteriology* 158(1):115–120.

* cited by examiner

*Primary Examiner*—Rodney P Swartz
*Assistant Examiner*—Khatol S Shahnan-Shah
(74) *Attorney, Agent, or Firm*—Saliwanchik, Lloyd & Saliwanchik

(57) ABSTRACT

A method for identifying antimicrobial agents comprises the steps of: (i) contacting a sample containing non-mammalian PPAT enzyme with a suitable substrate and a potential antimicrobial or antiprarasitic agent, under suitable conditions; (ii) measuring the activity of the PPAT enzyme; (iii) comparing the activity of the enzyme to that of a reference sample lacking the agent; and (iv) selecting an agent that reduces the activity of the PPAT enzyme.

3 Claims, No Drawings

```
                            SEQUENCE LISTING

<160> NUMBER OF SEQ ID NOS: 8

<210> SEQ ID NO 1
<211> LENGTH: 480
<212> TYPE: DNA
<213> ORGANISM: Escherichia coli

<400> SEQUENCE: 1
atgcaaaaac gggcgattta tccgggtact ttcgatccca ttaccaatgg tcatatcgat      60
atcgtgacgc gcgccacgca gatgttcgat cacgttattc tggcgattgc cgccagcccc     120
agtaaaaaac cgatgtttac cctggaagag cgtgtggcac tggcacagca ggcaaccgcg     180
catctgggga acgtggaagt ggtcgggttt agtgatttaa tggcgaactt cgcccgtaat     240
caacacgcta cggtgctgat tcgtggcctg cgtgcggtgg cagattttga atatgaaatg     300
cagctggcgc atatgaatcg ccacttaatg ccggaactgg aaagtgtgtt tctgatgccg     360
tcgaaagagt ggtcgtttat ctcttcatcg ttggtgaaag aggtggcgcg ccatcagggc     420
gatgtcaccc atttcctgcc ggagaatgtc catcaggcgc tgatggcgaa gttagcgtag     480

<210> SEQ ID NO 2
<211> LENGTH: 159
<212> TYPE: PRT
<213> ORGANISM: Escherichia coli

<400> SEQUENCE: 2

Met Gln Lys Arg Ala Ile Tyr Pro Gly Thr Phe Asp Pro Ile Thr Asn
1               5                   10                  15

Gly His Ile Asp Ile Val Thr Arg Ala Thr Gln Met Phe Asp His Val
                20                  25                  30

Ile Leu Ala Ile Ala Ala Ser Pro Ser Lys Lys Pro Met Phe Thr Leu
            35                  40                  45

Glu Glu Arg Val Ala Leu Ala Gln Gln Ala Thr Ala His Leu Gly Asn
        50                  55                  60

Val Glu Val Val Gly Phe Ser Asp Leu Met Ala Asn Phe Ala Arg Asn
65                  70                  75                  80

Gln His Ala Thr Val Leu Ile Arg Gly Leu Arg Ala Val Ala Asp Phe
                85                  90                  95

Glu Tyr Glu Met Gln Leu Ala His Met Asn Arg His Leu Met Pro Glu
                100                 105                 110

Leu Glu Ser Val Phe Leu Met Pro Ser Lys Glu Trp Ser Phe Ile Ser
            115                 120                 125

Ser Ser Leu Val Lys Glu Val Ala Arg His Gln Gly Asp Val Thr His
        130                 135                 140

Phe Leu Pro Glu Asn Val His Gln Ala Leu Met Ala Lys Leu Ala
145                 150                 155

<210> SEQ ID NO 3
<211> LENGTH: 45
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence
```

```
<400> SEQUENCE: 3
gctctagagc tatgaaggag atatacatat gcaaaaacgg gcgat                45

<210> SEQ ID NO 4
<211> LENGTH: 25
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence

<400> SEQUENCE: 4
cgggatccaa cgctacgcta acttc                                      25

<210> SEQ ID NO 5
<211> LENGTH: 38
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence

<400> SEQUENCE: 5
aaggaaaaaa gcggccgcaa cgtaaaattc cgctggtg                        38

<210> SEQ ID NO 6
<211> LENGTH: 42
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence

<400> SEQUENCE: 6
tgtttaagtt tagtggatgg ggggatcgaa agtacccgga ta                   42

<210> SEQ ID NO 7
<211> LENGTH: 44
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence

<400> SEQUENCE: 7
cccatccact aaacttaaac agtcacccat ttcctgccgg agaa                  44

<210> SEQ ID NO 8
<211> LENGTH: 30
<212> TYPE: DNA
<213> ORGANISM: Artificial sequence
<220> FEATURE:
<221> NAME/KEY: misc_feature
<222> LOCATION: ()..()
<223> OTHER INFORMATION: Primer sequence

<400> SEQUENCE: 8
tcccccgggc taccgtttaa gcgaccaacc                                 30
```

PRODUCTION AND USE OF ANTIMICROBIAL AGENTS

CROSS-REFERENCE TO A RELATED APPLICATION

This application is a National Stage Application of International Application Number PCT/GB99/03132, filed Sep. 21, 1999 and claims priority to United Kingdom application No. 9820538.8, filed Sep. 21, 1998.

FIELD OF THE INVENTION

This invention relates to the production of antimicrobial agents for use in therapy and to methods for identifying suitable antimicrobial agents.

BACKGROUND TO THE INVENTION

It is now widely recognised that conventional antibiotics are becoming less effective in treating microbial infections due to the spread of resistant microbial strains. It is therefore important to develop new antimicrobial agents to treat infection.

An approach to identifying potential antimicrobial agents is to select a suitable target, the inhibition of which will result in the eradication of the microbe with minimum effects on the host.

An important requirement is that the target should be essential to the viability of the microbe, as often a microbe will have an alternative mechanism for carrying out the function of the target. For example, the microbe may utilise a different enzyme or a different pathway to by-pass the inhibition of the target.

In considering novel single targets (e.g. those not part of large assemblies such as ribosomes) an important consideration is whether the target, usually an enzyme, is unique to bacteria. If so, its properties and suitability for the design or discovery of useful inhibitors can be exploited without detrimental effects on the host. Other targets, such as dihydrofolate reductase (DHFR), are common to both bacterial and animal cells and therefore selective inhibition of the microorganism is essential if dose-dependent toxicity to the host is to be avoided. The antimicrobial drug trimethoprim is a useful example of a clinically-valuable DHFR inhibitor which competes with substrate (dihydrofolate) and is bound 50,000-fold more tightly by bacterial than mammalian forms of DHFR.

There are therefore several considerations that must be made when selecting a suitable target, and these considerations make the selection of a suitable target difficult.

Therefore, there is a recognised need for identifying and characterising suitable targets that may be useful in antimicrobial therapy. In particular, there is a need for identifying targets that may be used to screen compounds for antimicrobial activity which can be used to prevent, reduce or eradicate infections.

SUMMARY OF THE INVENTION

The present invention is based on the realisation that enzymes involved in co-enzyme A (CoA) synthesis may be suitable targets for antimicrobial or antiparasitic agents. In particular, it has been appreciated that the enzyme phosphopantetheine adenylyltransferase (PPAT) is a suitable target to inhibit the Coenzyme A synthetic pathway, thereby preventing bacterial growth. The suitability of PPAT as an antimicrobial or antiparasitic target is based, at least in part, on an appreciation that the differences in the PPAT enzyme in mammalian and bacterial systems may be exploited to provide selective inhibition of the bacterial form. In particular, the mammalian form exists as a bifunctional enzyme complex with dephospho-CoA kinase (dCoAk), whereas the bacterial form contains separate PPAT and dCoAk. Similar structural differences are found in yeast, fungi and parasitic forms of PPAT.

Therefore, the present invention relates to the use of bacterial or similar PPAT enzyme to select for antimicrobial agents. According to the present invention, a method for identifying antimicrobial agents, comprises the steps of:

(i) contacting a sample containing non-mammalian PPAT enzyme with a suitable substrate and a target compound under suitable conditions;

(ii) measuring the activity of the PPAT enzyme;

(iii) comparing the activity of the enzyme to that of a reference sample lacking the target compound; and (iv) selecting those targets compounds that reduce the activity of the PPAT enzyme.

In a further bodiment, the present invention proposes the use of compounds capable of inhibiting the PPAT enzyme at a cellular or tissue concentration of less than 10 $\mu$M in antimicrobial therapy. In particular, the compounds may be used in the treatment of infection by *E. coli, Pseudomonas aeruginosa, Streptococcus pneumoniae, Haemophilus influenzae, Mycobacterium tuberculosis, Neisseria meningitidis* and *Staphylococcus aureus*, or any other pathogenic bacteria where PPAT activity is required for CoA synthesis.

According to a further embodiment, a substantially pure non-mammalian PPAT enzyme, or active fragment thereof, is used in a method for the identification of an antimicrobial or antiparasitic agent. Similarly, a gene encoding a non-mammalian PPAT enzyme may be used in a method for the identification of an antimicrobial or antiparasitic agent.

DESCRIPTION OF THE INVENTION

According to the present invention, methods for treating bacterial infection comprise selectively inhibiting the non-mammalian form of phosphopantetheine adenylyltransferase (PPAT). It has been recognised that this enzyme, also known as dephospho-CoA pyrophosphorylase, has particular characteristics which make it suitable as a target for inhibiting bacterial growth.

The term "PPAT enzyme" refers to the complete catalytically-active PPAT enzyme, or to fragments of the enzyme that retain catalytic activity. The enzyme may be used in the methods of the present invention either immobilised on a solid support or in solution.

The term "microbial" relates to any microorganism that is capable of causing infection, e.g. bacterial, fungal and yeast. In particular the term relates to bacterial organisms, especially those implicated in infectious disease, for example, *E. coli, Pseudomonas aeruginosa, Streptococcus pneumoniae, Haemophilus influenzae, Mycobacterium tuberculosis, Neisseria meningitidis* and *Staphylococcus aureus*.

PPAT enzymes may also be derived and purified from parasitic organisms which require the enzyme activity for CoA synthesis.

The term "target compound" relates to any suitable agent that may be used as an inhibitor of PPAT activity. The compound may be biological, i.e. a protein or peptide that binds to and inhibits PPAT activity or alters the conformation of the enzyme in such a way as to block the substrate from the catalytic region, or may be a chemical compound.

In either instance, the compound may be found naturally or may be synthesised. Suitable synthesis techniques will be apparent to those skilled in the art.

Possible target compounds may be chemically related to the natural substrates of PPAT, i.e. phosphopantetheine and ATP. Such substrates are converted to products at the catalytic centre of the enzyme, and so it is reasonable to assume that derivatives or analogues of such substrates may be identified which lead to selective inhibition of non-mammalian PPAT. In addition, compounds unrelated to the natural substrates may also be useful inhibitors. It is also envisaged that the inhibitors of PPAT activity may not act directly on the PPAT enzyme, but may instead act at the genetic level to block further production of PPAT.

The term "activity" refers to the natural biological activity of the PPAT enzyme. Usually this activity takes the form of the transfer of the reactive adenylyl group from ATP to phosphopantetheine, yielding dephospho-CoA. However, enzyme reactions seldom proceed only in the forward direction, and the reverse direction may also be utilised for determining the activity of PPAT. Use of the reverse reaction may be beneficial as it is linked to the formation of ATP which may then be utilised in fluorescence or luminescence detection techniques, for example the ATP-dependent oxidation of luciferin by luciferase with the concomitant production of light. Other ways of measuring PPAT activity will be apparent to those skilled in the art and will be useful in the methods of the present invention.

The term "therapy" refers to the treatment of diseases arising as a result of infection, not only by bacteria but also by fungi or parasites for which PPAT is required for the synthesis of CoA.

The term "medicament" refers to any suitable pharmaceutical composition. Specifically, it refers to a composition comprising the anti-infective agent in any suitable excipient or diluent, and also to different formulations required for different methods of administration. For example, the medicament may be formulated for oral administration, or may be formulated for intravenous administration.

Suitable excipients or diluents will be apparent to the skilled person, and the amount of antimicrobial agent present in the formulation can be easily determined, and will depend, in part, on the activity of the antimicrobial agent, and its side-effect profile.

The PPAT enzyme that is proposed for use in the present invention may be any microbial or parasitic PPAT enzyme. The existence of PPAT enzymes are known and are disclosed in, for example, Abiko et al, J. Biochem. (1967); 61:309 and Suzuki et al., J. Biochem. (1967); 62:642. As discussed previously, microbial PPAT is very different from mammalian PPAT, which is not proposed for use in the present invention, other than as a control for identifying inhibitory compounds that are selective for the microbial or parasitic form. Particularly preferred PPAT enzymes for use in the present invention include any gram-positive or gram-negative bacterial organism, *E. coli, Pseudomonas aeruginosa, Streptoccoccus pneumoniae, Haemophilus influenzae, Mycobacterium tuberculosis, Neisseria meningitidis, Staphylococcus aureus* or other examples of pathogenic bacteria. The deduced amino acid sequence of the PPAT enzyme is well conserved in many different bacterial species, and so selecting an enzyme from one organism may permit an extrapolation of results to other organisms. However, it may be preferable for optimal therapeutic effect if the enzyme is selected from a particular bacterial species causing infection.

The PPAT enzyme may be purified from the organism using any conventional method. Suitable methods are known to those skilled in the art and include those methods disclosed in Worrall et al, Biochem. J. 1983; 215: 153–157. The purification may be carried out using protein purification techniques, e.g. ion-exchange chromatography and gel filtration techniques. The PPAT enzyme may also be produced by solid phase synthesis, or by recombinant DNA methods using the cloned PPAT gene or a fragment of this gene.

The PPAT gene is termed kdtB, and the sequence is available from DDBJ/EMBL/GenBank. Although the sequence is known, the function of the gene was thought initially to be linked to an aspect of the lipopolysacchanide assembly (Clementz and Raetz, J. Biol. Chem., 1991; 266:9687–9696), but has now been identified as PPAT, by the present inventors.

The following Examples illustrate the invention.

EXAMPLE 1

Construction of a Vector for Expressing the *E. coli* PPAT Gene in *E. coli*

The PPAT gene (SEQ ID NO. 1) was produced by the polymerase chain reaction (PCR) using standard methods and oligonucleotide primers targeted to the 5' (SEQ ID NO. 3) and 3' (SEQ ID NO. 4) ends of the coding sequence of the gene. The primer for synthesis-at the 3' end contained a BamHI restriction site while that for the 5' end contained an XbaI site for cloning into the vector pUC19. Following digestion of both the PCR product and the vector by BamHI and XbaI, the fragment encoding the gene was ligated into plasmid pUC19 to give the expression construct pUC/PPAT.

Purification of *E. coli* PPAT

All steps were carried out at 4° C., except steps (5), (6) and (7) which were carried out at room temperature.

(1) *E. coil* JM101 harbouring (pUC/PPAT) were grown and harvested by centrifugation. Cell paste (69.5 g) was resuspended in 70 ml of 50 mM Tris-HCl buffer pH 8.0, containing 5 mM DTT, 0.2 mM dithiothreitol and 0.2 mM phenylmethylsulphonyl fluoride and 5 μg Dnase. The cells were broken by repeated bursts of sonication for 60s and cell debris was removed by centrifugation at 30,000×g for 20 min.

(2) The supernatant was applied to a DEAE-Sephacel column (80 ml bed volume), equilibrated with 25 mM Tris-HCl buffer, pH 8.0, containing 5 mM dithiothreitol (TD buffer). Unbound proteins were washed from the column with TD buffer, and bound proteins were then eluted with a gradient of 0 to 0.5 M NaCl in TD buffer. Fractions containing PPAT activity were combined and concentrated to 25 ml by ultrafiltration through a 10000 Da cut-off membrane. The concentrated sample was dialysed overnight against 1.5 L, 10 mM Hepes-NaOH buffer, pH 8.0, containing 10 mM $MgCl_2$ and 0.5 mM dithiothreitol (HMD buffer).

(3) The dialysed sample was loaded onto a Procion Red-Sepharose column (40 ml bed volume) equilibrated with HMD buffer. The majority of the PPAT sample did not bind to this column, and was recovered, concentrated by ultrafiltration and desalted using a column of Sephadex G-25 equilibrated in HMD buffer. This step is necessary to remove a low molecular weight compound that interferes with binding of PPAT to Procion Red-Sepharose.

(4) The desalted material was reapplied to a column of Procion Red-Sepharose, and eluted with a 0 to 1.0 M gradient of NaCl in HMD buffer. Fractions containing PPAT activity were combined and dialysed overnight against 1.5 L 10 mM Hepes-NaOH buffer, pH 8.0 containing 0.5 mM dithiothreitol (HD buffer).

(5) The dialysed sample was applied to a Resource Q column (1 ml bed volume, from Pharmacia) and eluted with a gradient of 0.2 to 0.4 M NaCl. Fractions containing PPAT activity were combined and desalted on a PD10 column (Pharmacia).

(6) Step (5) was repeated with the exception of the desalting procedure.

(7) The PPAT sample from step (6) was applied to HiPrep Sephacryl S-100 (Pharmacia) gel filtration column equilibrated in 10 mM Hepes-NaOH buffer, pH 8.0 containing 0.15 M NaCl and 0.5 mM dithiothreitol. Fractions containing PPAT activity were eluted in this buffer and stored at −80° C. The amino acid sequence for the PPAT enzyme is shown as SEQ ID NO. 2.

EXAMPLE 2

Assay for Inhibitors of E. coli PPAT

The activity of the PPAT enzyme was assayed by monitoring the pyrophosphate dependent cleavage of dephosphocoenzyme A which produced ATP and phosphopantetheine. The reaction contains in a final volume of 1 ml: 50 mM Tris-HCl containing 2 mM tetrasodium pyrophosphate, pH 8.0; 1 mM dithiothreitol; 1 mM NADP; 2 mM $MgCl_2$; 5 mM glucose; 9 µg yeast hexokinase; and 7 µg yeast glucose 6-phosphate dehydrogenase. Reactions were monitored spectrophotometrically at 25° C. by following the increase in absorbance at 340 nm.

Inhibition studies were carried out using the reaction conditions described above. Test compounds were added to a final concentration of 0.05 mM, and the percentage inhibition determined by comparison with a control in which no test inhibitor is present.

In a test using 1,2,3,6,7,8-hexahydropyrene-1,3,6,8-tetraone, this compound inhibited E. coli PPAT, giving approximately 60% inhibition at 0.05 mM.

Example 3 describes a gene knock-out experiment which demonstrates that the PPAT enzyme is essential for the survival of the bacterium.

EXAMPLE 3

The basic procedure for carrying out the gene knock-out experiment is as described in Link et al., Journal of Bacteriology; 1997, October:6228–6237. The experiment is based on gene replacement by homologous recombination between a bacterial chromosome and a plasmid carrying a mutated target PPAT (kdtB) gene which is unable to encode active protein. The replication ability of the plasmid is temperature sensitive and at the non-permissive temperature of 43° C., the bacterial cells will only be able to grow if the plasmid integrates into the chromosome by homologous recombination. The plasmid can be excised by means of a second recombination event at the permissive temperature of 30° C. Depending on the position of the second recombination event, the chromosome retains either wild-type sequence or the altered sequence from the plasmid. Analysing the products will reveal whether the wild-type gene is essential for viability. If the gene is essential, all viable bacteria will contain an unmutated or wild-type version of the gene.

All strains were grown in LB media with the appropriate antibiotic selection. The concentrations of antibiotics for selection were 100 µg/ml (ampicillin) and 30 µg/ml (chloramphenicol). For selection against sacb, LB medium was supplemented with sucrose to a final concentration of 5% sucrose (w/v).

Plasmids were prepared using QIAGEN™ mini or midi-plasmid purifications kts. The plasmid pKO3 and E. coli K12 EMG2 strain were provided by George M. Church (harvard Med. School). A 1.7 kb fragment containing the deleted kdtB gene (kdtB-X) was created using PCR in two steps using a PCR amplification kit (Boehringer Mannheim) as follows, First, a single E. coli K12 colony was boiled for 5–7 min in 50 µl water, centrifuged and 1 µl of the supernatant was collected for use as the template for the initial PCR reactions.

Two PCR reactions were used to amplify different regions of the kdtB gene, which were subsequently joined to create as in-frame deletion mutant.

The PCR reactions were carried out in a 25 µl final volume. In the first reaction, primer A (SEQ ID NO. 5) containing a Not I site and primer B (SEQ ID NO. 6) were used to amplify one section of the PPAT gene. In the second PCR reaction, primer C (SEQ ID NO. 7) and primer D (SEQ ID NO. 8) containing a SmaI site were used to amplify a second section of the PPAT gene. The primers were used at a final concentration of 100 pM. The PCR mixture was denatured at 95° C. for 4 min. The thermal cycler profile was 30 s at 95° C., 30 s at 48° C., and 2 min at 72° C. This cycle was repeated 30 times and a final 7 min extension step at 72° C. was followed by 4° C. hold. A sample of each of the two PCR products (4 µl) was analysed on a 1% agarose gel and the remainder was recovered in 30 µl 50% EB buffer, using the QIAGEN™ PCR kit. In a final PCR reaction, 1 µl of each of the recovered PCR products was combined and used as the template.

It was possible to combine the two reaction products as primers B and C (incorporated into the respective products) contain complementary ends and permit hybridisation to occur between the products. The final PCR reactions were carried out in 50 µl final volumes using a similar PCR cycle as above but using only the outside primers A and D.

The 1701 bp PCR framen (gene deletion) obtained from the final polymerase reaction was cloned into PCR cloning vector TA (INVITROGEN™). The clone containing the insert was verified by restriction mapping and DNA sequence analysis. The Not I and Sma I digested fragment was then cloned into Not I and Sma I digested PKO3.

Clones containing the deleted gene (pkdtB-X) were identified. The plasmid pKO3-kdtB-X was used for all the knockout experiments.

The plasmid pKO3-kdtBX containing the deleted kdtB gene in the pKO3 gene replacement vector was transformed by electroporation into E. coli K12 EMG2 electrocompetent cells. The cells were plated on pre-warmed Chloramphenicol-LB plates and incubated at 43° C. (non-permissive) to select for plasmid-linked resistance to chloramphenicol, arising from chromosomal integration. Cells were also incubated at 30° C. (permissive) to measure the efficiency of transformation. Five to ten colonies were picked from the 43° C. plates into 1 ml of LB broth, serially diluted, and immediately plated at 30° C. on 5% (w/v) sucrose-LB plates and at 43° C. on Cam-LB plates. The 5% sucrose plates were replica plated to Cam-LB plates at 30° C. to test for the loss of pKO3. The gene replacement was confirmed by PCR (using primers flanking pKO3).

The results showed that amongst the survivors there was a complete absence of sucrose-resistant and chloramphenicol-sensitive clones containing only the deleted kdtB construct. The result indicates the essential nature of the kdtB gene (specifying PPAT) for the viability of the strain of E. coli used in the experiment.

What is claimed is:

1. A method for identifying an agent having the ability to inhibit a PPAT enzyme, comprising the steps of:
   (i) contacting a sample containing a PPAT enzyme consisting of SEQ ID NO: to 2 with a suitable substrate and an agent to be evaluated;
   (ii) measuring the activity of the PPAT enzyme;
   (iii) comparing the activity of the enzyme to that of a reference sample lacking the agent; and
   (iv) selecting an agent that reduces the activity of the PPAT enzyme.

2. The method according to claim 1, wherein the agent does not inhibit a mammalian PPAT enzyme.

3. The method according to claim 1, wherein the agent reduces the activity of the PPAT enzyme by at least 20% when said agent is present at a concentration of less than 100 $\mu$M.

* * * * *